United States Patent
Greiser

(10) Patent No.: US 11,721,431 B2
(45) Date of Patent: Aug. 8, 2023

(54) MEDICAL USER INTERFACE

(71) Applicant: Siemens Healthcare GmbH, Erlangen (DE)

(72) Inventor: Andreas Greiser, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 220 days.

(21) Appl. No.: 17/104,393

(22) Filed: Nov. 25, 2020

(65) Prior Publication Data

US 2021/0158948 A1    May 27, 2021

(30) Foreign Application Priority Data

Nov. 27, 2019   (EP) ..................................... 19211895

(51) Int. Cl.
*G16H 40/20* (2018.01)
*A61B 34/00* (2016.01)
(Continued)

(52) U.S. Cl.
CPC ............. *G16H 40/20* (2018.01); *A61B 34/25* (2016.02); *A61B 90/361* (2016.02); *A61B 90/37* (2016.02); *A61B 90/98* (2016.02); *G06K 7/10297* (2013.01); *G16H 10/20* (2018.01); *G16H 15/00* (2018.01); *G16H 30/20* (2018.01);
(Continued)

(58) Field of Classification Search
CPC combination set(s) only.
See application file for complete search history.

(56) References Cited

U.S. PATENT DOCUMENTS 8,331,530 B2    12/2012  Butzine et al.
8,767,917 B2*   7/2014   Ruchala ................. G16H 50/50
                                                              378/65
(Continued)

FOREIGN PATENT DOCUMENTS

EP          3540740 A1      9/2019
WO     WO 2015181636 A2    12/2015

OTHER PUBLICATIONS

C. Yolcu, Gozde; Oztel, Ismail; Kazan, Serap; Oz, Cemil; Kannappan Palaniappan; et al., Facial expression recognition for monitoring neurological disorders based on convolutional neural network, Multimedia Tools and Applications 78.22: 31581-31603. Dordrecht: Springer Nature B.V. (Nov. 2019) (Year: 2019).*

(Continued)

*Primary Examiner* — Amber A Misiaszek
(74) *Attorney, Agent, or Firm* — Banner & Witcoff Ltd.

(57) ABSTRACT

A medical user interface for the combined use of at least two medical examination systems. The medical user interface includes a display data interface to connect to a display and to send medical display data to be displayed on the display, an input data interface to connect to an input device for receiving instructions of a user, a communication interface to a data connection with the medical examination systems, and a computer. The computer is designed to establish a data communication to the medical examination systems via the communication interface, and a) to create the display data and send the display data to the display, b) to process the instructions from a user, and c) to send control data to the medical examination systems or to receive and process medical examination data received from the medical examination systems.

19 Claims, 4 Drawing Sheets

(51) Int. Cl.
　　　*A61B 90/00*　　　(2016.01)
　　　*A61B 90/98*　　　(2016.01)
　　　*G16H 40/67*　　　(2018.01)
　　　*G16H 50/50*　　　(2018.01)
　　　*G16H 15/00*　　　(2018.01)
　　　*G16H 30/20*　　　(2018.01)
　　　*G16H 50/30*　　　(2018.01)
　　　*G16H 50/70*　　　(2018.01)
　　　*G16H 50/20*　　　(2018.01)
　　　*G16H 40/40*　　　(2018.01)
　　　*G16H 10/20*　　　(2018.01)
　　　*G06K 7/10*　　　(2006.01)
　　　*A61B 5/11*　　　(2006.01)

(52) U.S. Cl.
　　　CPC ............. *G16H 40/40* (2018.01); *G16H 40/67* (2018.01); *G16H 50/20* (2018.01); *G16H 50/30* (2018.01); *G16H 50/50* (2018.01); *G16H 50/70* (2018.01); *A61B 5/1112* (2013.01); *A61B 5/1128* (2013.01); *A61B 2562/0219* (2013.01)

(56) References Cited

U.S. PATENT DOCUMENTS

| 2001/0016822 | A1* | 8/2001 | Bessette | G06Q 90/00 |
| --- | --- | --- | --- | --- |
| | | | | 705/3 |
| 2004/0260577 | A1* | 12/2004 | Dahlin | G16H 50/20 |
| | | | | 705/2 |
| 2006/0173270 | A1 | 8/2006 | Weiner et al. | |
| 2011/0119224 | A1* | 5/2011 | Mangione-Smith | G16H 50/50 |
| | | | | 340/407.1 |
| 2014/0247153 | A1* | 9/2014 | Proud | H04W 4/21 |
| | | | | 340/870.09 |
| 2015/0237222 | A1 | 8/2015 | Haider et al. | |
| 2017/0086759 | A1 | 3/2017 | Eichler et al. | |
| 2018/0078222 | A1 | 3/2018 | Boettger et al. | |
| 2019/0282214 | A1 | 9/2019 | Park et al. | |
| 2020/0105400 | A1* | 4/2020 | Alvelda, VII | G16H 40/63 |
| 2020/0205748 | A1* | 7/2020 | Pautsch | A61B 5/7207 |

OTHER PUBLICATIONS

Von Kienlin, Markus et al. "Advances in Human Cardiac 31P-MR Spectroscopy: SLOOP and Clinical Applications", Journal of Magnetic Resonance Imaging, 2001, vol. 13, pp. 521-527.

Löffler R. et. al., "Localized Spectroscopy from Anatomically Matched Compartments: Improved Sensitivity and Localization for Cardiac 31P MRS in Humans", Journal of Magnetic Resonance 134, pp. 287-299, 1998.

Search Report dated Apr. 17, 2020 for European Patent Application No. 19211895.8.

* cited by examiner

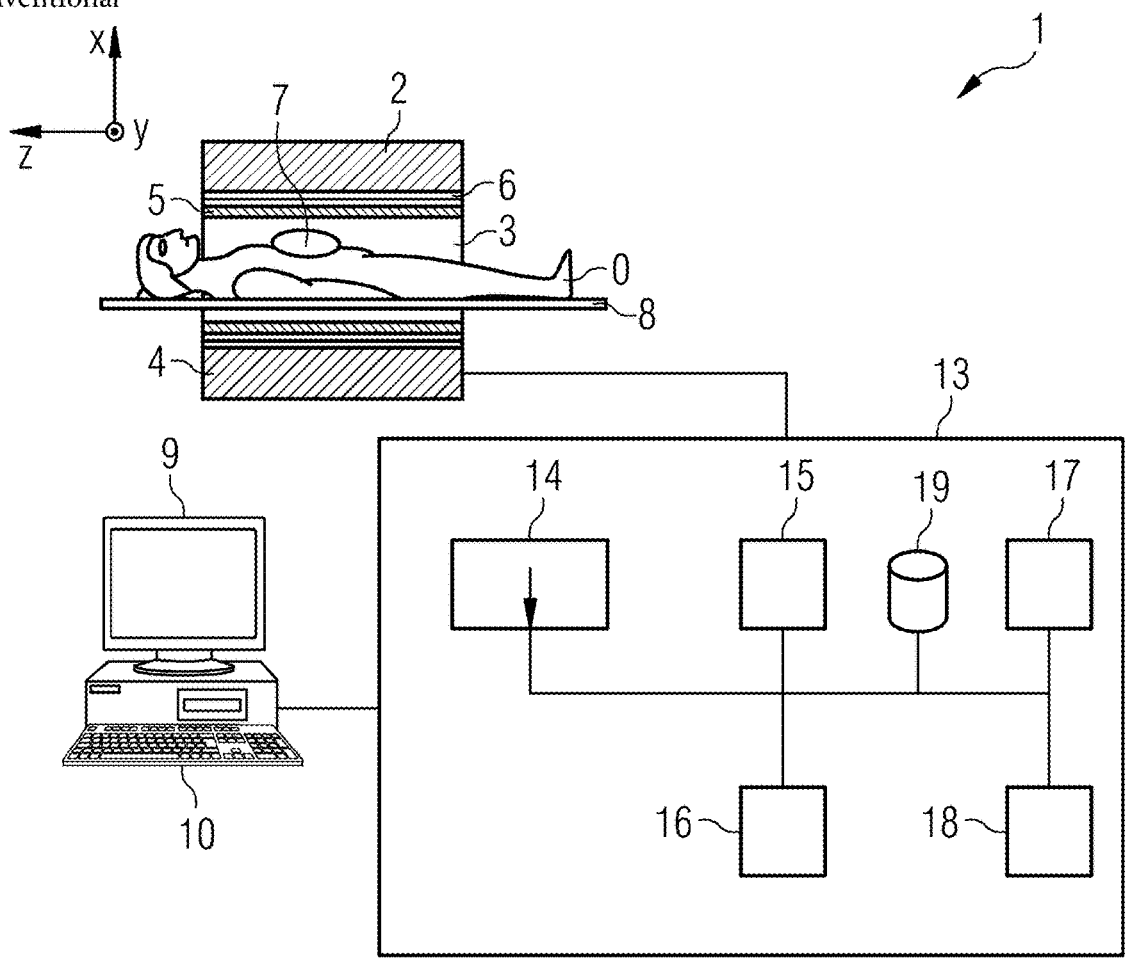
FIG 1
Conventional

MEDICAL USER INTERFACE

TECHNICAL FIELD

The disclosure describes a medical user interface, especially for medical image acquisition systems, as well as a method designed to operate such user interface.

BACKGROUND

The acquisition of medical data is necessary for modern medicine. Besides "simple" acquisition like measuring temperature or blood pressure, there are more complex data measured with medical examination devices, which are often medical image acquisition devices like e.g. magnetic resonance imaging ("MRI") devices or computer-tomography ("CT") devices. Typically these devices are individually controlled and produce vast amounts of data.

Usual examination devices, such as imaging modalities (even different MRI scanners or CT scanners), use some kind of specific user interface and are implemented as independently controlled units, i.e. these modalities have individually organized consoles requiring modality specific knowledge.

This is insignificant in the case only one device is used, e.g. in a private doctor's surgery, but a major drawback in the case a whole "fleet" of different examination devices is used, e.g. in a hospital, since every single examination device has to be controlled in an individual way and sends data to individual data-receiving units.

Therefore, while using different scanners the operator has to use independent scanner controls and different user interfaces. To some extent there have been made efforts to harmonize the UI of different instances of a scan modality or even of different modalities within a multi-modality portfolio or to integrate different modalities into one scanner (e.g., mMR, PET-CT, . . . ) using a single control unit. Nevertheless the operator has to be familiar with the different acquisition techniques and run the different acquisitions, typically subsequently and independently.

SUMMARY

It is the object of the present disclosure to improve the known devices and methods to facilitate an improvement in medical data acquisition, especially in medical image acquisition. A special object is to solve the question, how a single user interface could be designed that is able to encompass all (or most) available modalities and/or scanner instances, e.g. also high end vs. low end scanners and virtually merging all available image data and information into a single patient representation, possibly involving a digital twin or enabling an operator to easily control different devices.

A medical user interface according to the disclosure for the combined use of at least two medical examination systems, comprises the following components:

a. a display data interface designed for connecting to a display and for sending medical display data to be displayed on the display, b. an input data interface designed for connecting to an input device for receiving instructions of a user, c. a communication interface designed for a data connection with the medical examination systems, and d. a computing unit designed to establish a data communication to the medical examination systems via the communication interface and designed i. to create the display data and send it to the display (via the display data interface), ii. to process the instructions from a user (via the input data interface), and iii. to send control data to the medical examination systems and/or to receive and process medical examination data received from the medical examination systems.

The medical user interface ("UI") may be a physical device (e.g. a tablet computer) or a software module (e.g. an app or a cloud system). It serves for the combined use of at least two medical examination systems. This means that it is able to communicate with both examination systems, e.g. an MRT-apparatus and a CT-apparatus, and can receive and "understand" data send from both examination systems and/or send control data to both examination systems that is "understood" by both systems.

The data interfaces, and especially also the communication interface may be realized by the same hardware. For example, in the case the user interface is a cloud system, the data/communication interfaces could be realized as network interfaces (e.g. WLAN or LAN). However, in the case the UI is a program running on a computing unit (e.g. a tablet computer), the interfaces could be different interfaces, like a graphical databus for the display data interface, a databus connection with a touch display (or another input device) for the input data interface and a network interface for the connection interface. However, the communication interface could also be wire-bound (e.g. an USB-interface) for connecting the UI to a system by data-wire.

The display data interface is designed to connect to a display (one or more) and for sending medical display data to be displayed on the display. The computing unit just has to provide data to this display data interface and it is preferably automatically displayed on the display (if a display is connected).

The input data interface is used to receive instructions from a user for the operation of the computing unit. The display data interface and the input data interface may be physical the same bidirectional data interface, as indicated above. The data interface could be designed to connect to a plurality of (especially different) input devices.

The communication interface is used to establish a data connection with the medical examination systems. It is used to receive data from and/or send data to the two or more (all) medical examination systems.

The computing unit is designed to establish a data communication to the medical examination systems via the communication interface. Thus, the communication interface provides the infrastructure and the computing unit produces the data send to and/or processes the data received from the examination systems. The computing unit creates the display data and sends it to the display via the display data interface and processes the instructions received from a user via the input interface. Furthermore, the computing unit is designed to send control data to the medical examination systems and/or to receive and process medical examination data received from the medical examination systems via the communication interface.

The user interface could comprise more units, especially a control unit for controlling an examination system and/or a scanner.

The computing unit as well as the data interfaces could be realized by a software module or by a physical unit.

This UI provides the opportunity to make different modalities look the same from the user UI. Thus, the same operator can handle various modalities with one single device. Such UI may trigger the integration of a patient- and/or operator centric control frontend covering multiple modalities or scanner instances, leveraging a multi-modality multi-instance scanner cluster integrating multiple imaging contrasts into a moving digital twin represented in a single common user control unit. These preferred aspects are further described below.

A method according to the disclosure is designed to operate a medical user interface according to the disclosure. It is also designed for the combined use of at least two medical examination systems (as is the UI) and comprises the following steps:

a. determining the state of an input device and in the case an instruction of a user is received, producing an output based on the instruction, b. sending control data based on an instruction to a medical examination system and/or receiving and processing medical examination data (e.g. images or information from other examinations) from a medical examination system, and c. displaying the processed medical examination data and/or data from a medical examination system.

The state of an input device is received via the input data interface. If an input occurred, input data will be received, if not, no data will be received. If a user enters an instruction, this instruction is sent via the input data interface to the computing unit. Then, in the case an instruction of a user is received an output is produced based on the instruction. Such instruction can be a control instruction, e.g. to start a specific examination with an examination unit, resulting in control data being sent to the examination system. Such instruction can be an instruction to display special data, for example, of an examination, resulting in a displaying of the requested data on the display (or more accurately resulting in the sending of the respective data via the display data interface). Thus, the displayed data preferably depends on an instruction. The output will then be the displayed data.

One important task of the method is sending control data to a medical examination system and/or receiving and processing medical examination data from a medical examination system. The control data may be an examination protocol (e.g. a MRI-protocol) or data to configure an examination system and a signal to start an examination. In the case medical examination data is received, it should be processed for displaying the data.

Last, the method comprises the step of displaying the processed medical examination data. Alternatively or additionally, data from a medical examination system is displayed, since this provides a visible feedback of the system. Thus, besides the display of processed data, also a feedback from a medical examination system can be displayed, such as parameters for examination or a simple information about the progress of an examination.

A device according to the disclosure is designed to communicate with a user interface according to the disclosure and/or to perform a method according to the disclosure. The device preferably comprises the user interface, e.g. as a software or hardware module.

A medical examination system according to the disclosure is designed to establish a data connection with a device/UI according to the disclosure. It is preferably designed to receive and use control data from the device/UI and/or to send examination data to the device/UI. Hence, the medical examination system is designed to communicate with the UI according to the disclosure.

Regarding the patient-side, the UI should be designed such that it collects and shows information about this specific patient (and especially no other patient, at least as long as it is not overridden). This information is preferably present information and/or new information added in the course of an examination.

Regarding the operator-side (with the term "operator" as well a technical operator as a medical operator is meant, e.g. a clinician, a physician, a doctor or else), the UI should be operator-specific and show information about patients (e.g. for clinicians) and/or examination systems (e.g. for technical operators, but also for clinicians). Preferably the UI is designed such that same issues are shown in the same manner. For example, if an avatar of a patient is shown it should be in the same position for every patient and e.g. women are shown with the same feminine avatar men should be displayed with the same masculine avatar.

Regarding the displaying of a patient for an operator, the UI should have a similar design as described above on behalf of the patient-side with the difference that the operator can choose different patients.

Regarding the control of examination systems, the UI should display the same technical issues of examination devices in the same manner to simplify operation of the examination systems. This could include that examination systems of the same type are displayed such, that same control icons are on the same locations independently of the actual examination device. This means that for example, MRI systems are always displayed in the same way and CT-systems are always displayed in the same way (but perhaps differently than MRI systems). It is also preferred that the same infrastructure units are always displayed in the same manner regarding control icons. "Infrastructure units" are units that provide the infrastructure for a scanner to scan properly. One could say that the infrastructure units deliver the "infrastructure medium" for the scanners. This infrastructure medium does not necessarily have to be a physical fluid (like cooling medium), but can be also energy or a data stream. Some exemplary infrastructure units are auxiliary units, such as a cooling unit, a sensor unit or a unit providing energy for auxiliary systems, power units, preferably a general power supply or a power amplifier, e.g. for RF or gradients in MRI or control units.

For the control there is preferably, besides the graphical feedback on the display, a number of functional layers that organize the communication with examination systems. It should be noted that not all layers have to be included in the UI. They also could be included in an examination system (that is then an examination system according to the disclosure as described above). One could say that layers described first are probably more "associated" with the UI and layers described later are probably more "associated" with an examination device.

First there is the input layer. It is connected very strongly to the display of the control icons (wherein "icons" could also be input windows for an alphanumerical input). With a choosing action (i.e. an activation or an alphanumerical input) of a control icon, an instruction is determined (e.g. "start examination"). A valid control icon may also be a part of the avatar of a patient. The operator may choose the head of the avatar by touching it on the touchscreen. This action activates the display of further icons, e.g. "MRI" and "CT". By pressing "MRI" the layer creates the instruction "MRI-scan of the head of patient X". Thus, an instruction may result in displaying another content or result in advancing to the next layer. Preferably, the UI is designed to include this layer.

Second there is an "instruction conversion layer". The instructions are here automatically converted in a data stream, which the respective examination system is able to "understand". For an MRI-system or CT-system this would be a measurement protocol (e.g. a pulse sequence). It should be noted that this layer may be divided in sub-layers, e.g. a layer specifying the exact examination (e.g. the contrast of an MRI measurement to be recorded) and the following sub-layer chooses the correct pulse sequence. Preferably, the UI or the medical examination system is designed to include this layer.

Third there is an "application layer" applying measurement signals based on the before mentioned data stream. Since the UI or the respective device may comprise infrastructure units (e.g. a RF-sender or power amplifiers of a gradient system of an MRI), it could directly apply measurement signals. However, typically this layer is present in an examination device, wherein the examination device must be designed to understand the data stream created by the second layer.

Some units or modules of the UI or the device mentioned above can be completely or partially realized as software modules running on a processor of a system or a device. A realization largely in the form of software modules can have the advantage that applications already installed on an existing system can be updated, with relatively little effort, to install and run these units of the present application. The object of the disclosure is also achieved by a computer program product with a computer program that is directly loadable into the memory of a device or a system (e.g. of a magnetic resonance imaging apparatus), and which comprises program units to perform the steps of the inventive method when the program is executed by the device or the system. In addition to the computer program, such a computer program product can also comprise further parts such as documentation and/or additional components, also hardware components such as a hardware key (dongle etc.) to facilitate access to the software.

A computer readable medium such as a memory stick, a hard-disk or other transportable or permanently-installed carrier can serve to transport and/or to store the executable parts of the computer program product so that these can be read from a processor unit of a device or a system. A processor unit can comprise one or more microprocessors or their equivalents.

Particularly advantageous aspects and features of the disclosure are given by the dependent claims, as revealed in the following description. Features of different claim categories may be combined as appropriate to give further aspects not described herein.

A preferred medical user interface is designed to provide at least one of the following two different modes.

The first mode is a patient mode, wherein access to a number of medical examination system is restricted and examination data is collected for an individual patient (only). Surely, the UI is also able to show the collected examination data. Thus, a patient can carry a device with the UI (e.g. a tablet computer) where an examiner can easily see all data collected for this specific patient. However, since patients usually must not operate examination systems, the access is preferably restricted.

The second mode is an operator mode, wherein access to medical examination systems and access to patient data is restricted according to access rights of a specific user (e.g. an operator or clinician). Thus, the UI can be carried by an operator and is able to control medical examination systems (e.g. define and start a MRI procedure). However, since usually not all operators are allowed to operate all examination systems or see all patient data, the access should be restricted, accordingly.

In a typical use case of the proposed concept, a patient is scanned with a first imaging modality, e.g. CT or MRI. When he moves to the department, the acquired image information is displayed at his bedside for an authorized person with the UI device available. Applying a point-of-care ("POC") modality at bedside an operator/clinician can perform additional scanning and watch the digital representation along with the new data, taking into account the different or even dynamic motion states.

As an alternative, the UI could be operator centered, i.e. each operator (or other role accessing the patient information) has its own device and gets access to the digital patient data of a specific patient by sensing its vicinity.

A preferred device/UI is designed such that the mode depends on the user logged in. Thus, an operator is preferably able to log in on a "patient device" and gets an operator mode UI.

A preferred medical user interface comprises a data interface designed to access sensor data, preferably from cameras, GPS-sensors, gyroscopes, RFID-sensors and/or sensors of a mobile computing or telecommunication device or an examination system. It is preferred that the computing unit is designed to track the position and/or the motion state of a patient or an operator position. For example, the existing imaging information can be rendered to the current motion state of the patient, possibly including additional physical tissue properties like stiffness, strain, proton density or water and fat content, etc. to allow the modeling of the tissue deformation based on the available data and motion sensor information.

In a preferred aspect according to the disclosure, components of the UI are part of a data-network, wherein preferably the data-network and scanners (e.g. the magnetic resonance imaging scanners or CT scanners) are in data-communication with each other, wherein the data-network preferably comprises parts of the internet and/or a cloud-based computing system, wherein preferably the UI according to the disclosure or a number of components of the UI is realized in or controlled by this cloud-based computing system. For example, the main components of the UI are aligned in form of a "server" that collects all relevant information about all relevant patients and is able to control all relevant examination systems. This "server" is able to connect and communicate with clients. These clients are display and input devices (e.g. tablet computers). The information that is sent to the display of a device and the control functions that can be executed by the device are depending on an individual allowance of this device. Thus, an operator can connect the device with the respective log-in information and the device can perform actions (display or control) depending from the access rights of the operator. Regarding a patient, the server recognizes a client assigned to a patient and sends only data to this client that is connected with this patient. It should be noted that it is preferred that an operator may log-in on a patient device and use this with his/her own access rights.

The method may also include elements of "cloud computing". In the technical field of "cloud computing", an IT infrastructure is provided over a data-network, e.g. a storage space or processing power and/or application software. The communication between the user and the "cloud" is achieved by means of data interfaces and/or data transmission protocols.

In the context of "cloud computing", in a preferred aspect of the method according to the disclosure, provision of data via a data channel (for example a data-network) to a "cloud" takes place. This "cloud" includes a (remote) computing system, e.g. a computer cluster that typically does not include the user's local machine. This cloud can be made available in particular by the medical facility, which also provides the medical imaging systems. In particular, the image acquisition data is sent to a (remote) computer system (the "cloud") via a RIS (Radiology Information System) or a PACS (Picture Archiving and Communication System).

According to a preferred method, in addition to examination data, patient specific information (i.e. non-examination information) is processed and displayed. This is done preferably initially or in addition to an examination. Regarding the graphical display, it is preferred that the patient is represented as a patient model, preferably as an avatar. The displayed examination data can be arranged such that it is located at the body region where the data was measured. Regarding images, they could be projected over the respective regions of the avatar. This has the advantage that the operator could see a patient centric user interface. It is preferred that before the first imaging scan has been performed, the avatar is already characterized by patient specific non-imaging information, e.g. patient details like size, gender, weight, age.

It is preferred that other clinical parameters than examination data is be available and also represented by the digital patient model. As soon as imaging information is available, the model is preferably adopted to be consistent with the image data.

The digital patient data or the examination data can represent information by physical parameters like tissue classes, densities and other physical properties like flow, strain, perfusion etc., along with some uncertainty indices, reflecting the fact that the data may be originating from different modalities, with different levels of quality, e.g. anatomical images from MRI vs dynamic real-time US imaging.

According to a preferred method, the patient is tracked, preferably in that the position or motion state of the patient is tracked or the examination and/or accommodation stations of the patient are tracked. With "tracking" not only a real-time measurement of the position (like GPS) is meant, but also the course of a patient through examinations. Since it is usually known, where the patient's bed and the examination systems are located, tracking can also comprise the knowledge whether the patient is in the bed or examined by a (defined) examination system.

Preferably, the tracking of the patient motion state is continued when moving from one modality scanner unit to another, e.g. after a comprehensive MRI scan the patient is moved to a point-of-care (POC) scanning at bedside where a portable US or CT scanner is used while the previously collected high resolution digital patient data is shown in the UI.

According to a preferred method, new examination data of a patient is added to present examination data. This has the advantage that with every new scan, the patient model (e.g. the avatar) is enriched with additional information. It is preferred that a part of the new examination data is combined with a part of the present examination data, wherein these parts pertain to the same medical environment, preferably the same disease, the same body region or the same examination procedure. Thus, the state of an organ can be updated by parts of new examination data referring to this organ. It is further preferred that examination data is combined with an individual time stamp. In one preferred aspect of the disclosure, besides image data information itself, an attribute of data actuality is added to the patient model.

According to a preferred method, the new examination data represent the difference of the current patient state according to the present examination data. This could be designated as "delta"-scanning. Preferably, there is displayed the change of the state relative to an initial measurement. It is preferred that this difference is measured directly based on the present examination data or calculated from the new examination data and the present examination data. It is further preferred that the new examination data are acquired with a point of care scanner and/or in the course of a point of care examination. Usually, a POC-scanner only detects the difference of the current patient state as compared to previously acquired examination data, possibly higher quality data. Hence it can be lower quality data but provide e.g. long-term follow-up information of a specific focus region where a finding was detected in the initial high quality scanning.

According to a preferred method, in the course of examination a combination of localization techniques, preferably a technique called "spatial localization with optimal point-spread function" (SLOOP), is applied. This method preferably comprises the following steps:

a. Deriving information about a compartment of a patient from the present examination data. The present examination data may be available from a high-resolution anatomical and functional scan. The term "high-resolution scan" especially means a scan with a higher resolution compared to the new examination data, especially more than 1.5 times, or even more that two times, higher.

b. Determining an optimal sampling pattern for an acquisition of new examination data based on the derived information. The "optimal sampling pattern" is preferably a predefined sampling pattern defined as optimal for a derived information. The derived information is preferably compared with predefined reference information that is connected with a predefined sampling pattern and the sampling pattern of the reference information with the highest similarity with the derived information is used. With that, e.g. the "per-compartment" information from a given organ or lesion segment can be detected in a lower resolution acquisition.

c. Controlling an examination of the patient with the determined sampling pattern.

The "SLOOP" technique has originally been developed for improved confidential localization in Spectroscopic MR Imaging (see, for example, Löffler et. al. "Localized Spectroscopy from Anatomically Matched Compartments: Improved Sensitivity and Localization for Cardiac 31P MRS in Humans", JMR 134, Issue 2, October 1998, Pages 287-299; or Kienlin et. al. "Advances in Human Cardiac 31P-MR Spectroscopy: SLOOP and Clinical Applications", JMRI 13:521-527, 2001). The high-resolution image information could be collected in a conventional scan, while the changed per-compartment information is sampled in the bedside scanner.

A preferred method comprises the steps:

a. providing or recording a first examination dataset from a first examination (especially from a high-quality scan), b. examining the first examination dataset for a local finding, c. determining a location in a patient of the local finding and/or defining a location in a patient by a user, and d. recording a second examination dataset with a second examination (especially a POC scan), wherein the region of interest of the second examination comprises the location in the patient.

It is preferred that the first examination dataset is more accurate than the second examination dataset. This means that the first dataset has a higher resolution and/or more data and or a smaller error and or a higher statistics than the second dataset (preferably more than 1.5 times higher or even more than two times higher).

For example, if in the initial scan (in the first examination dataset) an accumulation of a species is detected in a specific organ/compartment, the follow-up under therapy can be accomplished by a monitoring the affected organ or compartment using localized spectroscopic imaging or lower resolution MRI, facilitated by the a priori information from the high-quality scan.

Preferably, the high resolution/high-quality image data can be segmented into body tissue compartments automatically and the rendered compartment borders can be used in a bed side situation to optimize the POC Scanner acquisition protocol or to guide the measurement.

A preferred device is designed to be attachable to and detachable from a medical examination system and preferably also designed to accompany a patient while moving within a clinical environment and/or to be mountable on a patient bed. Especially in a cloud-based IT environment this could be a simple tablet computer or touch screen.

BRIEF DESCRIPTION OF THE DRAWINGS

Other objects and features of the present disclosure will become apparent from the following detailed descriptions considered in conjunction with the accompanying drawings. It is to be understood, however, that the drawings are designed solely for the purposes of illustration and not as a definition of the limits of the disclosure.

FIG. 1 shows a conventional MRI-apparatus.

In the diagrams, like numbers refer to like objects throughout. Objects in the diagrams are not necessarily drawn to scale.

DETAILED DESCRIPTION

Figure 2:
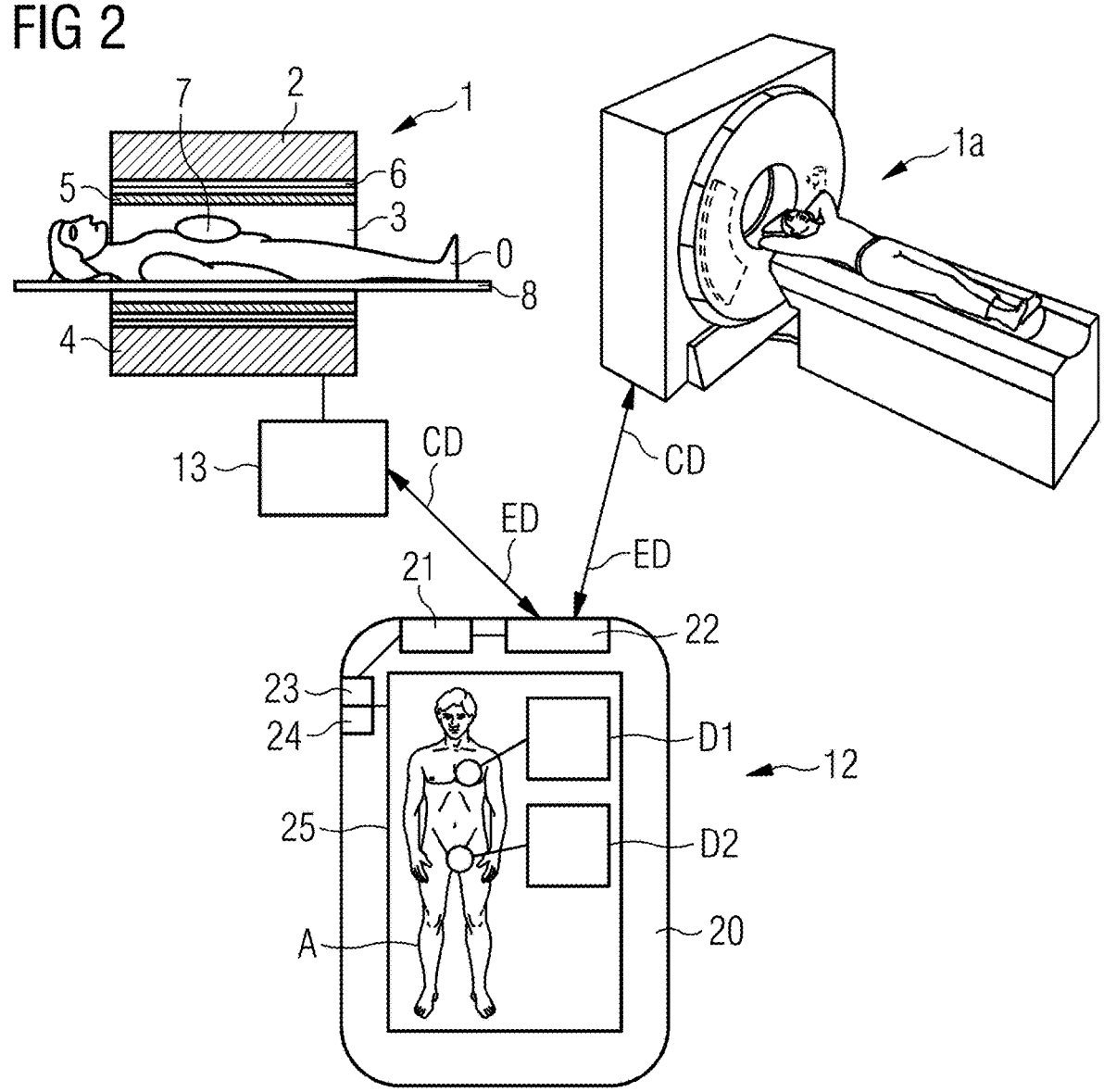
FIG. 2 shows a simplified aspect according to the disclosure.

FIG. 1 shows a schematic representation of a magnetic resonance imaging apparatus 1 ("MRI-apparatus"). The MRI apparatus 1 includes the actual magnetic resonance scanner (data acquisition unit) 2 with an examination space 3 or patient tunnel in which a patient or test person is positioned on a driven bed 8, in whose body the actual examination object is located.

The magnetic resonance scanner 2 is typically equipped with a basic field magnet system 4, a gradient system 6 as well as an RF transmission antenna system 5 and an RF reception antenna system 7. In the shown exemplary aspect, the RF transmission antenna system 5 is a whole-body coil permanently installed in the magnetic resonance scanner 2, in contrast to which the RF reception antenna system 7 is formed as local coils (symbolized here by only a single local coil) to be arranged on the patient or test subject. In principle, however, the whole-body coil can also be used as an RF reception antenna system, and the local coils can respectively be switched into different operating modes.

The basic field magnet system 4 is designed in a typical manner so that it generates a basic magnetic field in the longitudinal direction of the patient, i.e. along the longitudinal axis of the magnetic resonance scanner 2 that proceeds in the z-direction. The gradient system 6 typically includes individually controllable gradient coils in order to be able to switch (activate) gradients in the x-direction, y-direction or z-direction independently of one another.

The MRI apparatus 1 shown here is a whole-body apparatus with a patient tunnel into which a patient can be completely introduced. However, in principle the disclosure can also be used at other MRI apparatuses, for example with a laterally open, C-shaped housing, as well as in smaller magnetic resonance scanners in which only one body part can be positioned.

Furthermore, the MRI apparatus 1 has a central control device 13 that is used to control the MRI apparatus 1. This central control device 13 includes a sequence control unit 14 for measurement sequence control. With this sequence control unit 14, the series of radio-frequency pulses (RF pulses) and gradient pulses can be controlled depending on a selected pulse sequence.

To output the individual RF pulses of a pulse sequence, the central control device 13 has a radio-frequency transmission device 15 that generates and amplifies the RF pulses and feeds them into the RF transmission antenna system 5 via a suitable interface (not shown in detail). To control the gradient coils of the gradient system 6, the control device 13 has a gradient system interface 16. The sequence control unit 14 communicates in a suitable manner with the radio-frequency transmission device 15 and the gradient system interface 16 to emit the pulse sequence.

Moreover, the control device 13 has a radio-frequency reception device 17 (likewise communicating with the sequence control unit 14 in a suitable manner) in order to acquire magnetic resonance signals (i.e. raw data) for the individual measurements, which magnetic resonance signals are received in a coordinated manner from the RF reception antenna system 7 within the scope of the pulse sequence.

A reconstruction unit 18 receives the acquired raw data and reconstructs magnetic resonance image data therefrom for the measurements. This reconstruction is typically performed on the basis of parameters that may be specified in the respective measurement or control protocol. For example, the image data can then be stored in a memory 19.

Operation of the central control device 13 can take place via a terminal 10 with an input unit and a display unit 9, via which the entire MRI apparatus 1 can thus also be operated by an operator. MR images can also be displayed at the display unit 9, and measurements can be planned and started by means of the input unit (possibly in combination with the display unit 9), and in particular suitable control protocols can be selected (and possibly modified) with suitable series of pulse sequence PS as explained above.

The MRI apparatus 1, and in particular the control device 13, can have a number of additional components that are not shown in detail but are typically present at such apparatuses, for example a network interface in order to connect the entire apparatus with a network and be able to exchange raw data and/or image data or, respectively, parameter maps, but also additional data (for example patient-relevant data or control protocols).

FIG. 2 shows a simplified aspect according to the disclosure. In the upper left part there is shown an MRI-apparatus (s. e.g. FIG. 1) and in the upper right part a CT-apparatus 1a. These two apparatuses represent two different examination systems.

A tablet computer here represents a device 20 as well as a user interface 12 according to an aspect of the disclosure. The tablet computer comprises a display 25, here a touchscreen that acts as input device, as well. The tablet computer comprises a display data interface 23 designed for displaying data on the display 25, an input data interface 24 designed for connecting to an input device (here the touchscreen), a communication interface 22 designed for a data connection with the medical examination systems 1, 1a and a computing unit 21. It should be noted that the display data interface 23 and the input data interface 24 may be one single physical data interface.

The two double-headed arrows represent a data connection between the medical examination systems 1, 1a and the communication interface 22, wherein a data communication between the computing unit 21 and the examination systems 1, 1a occurs by examination data ED received and control data CD sent by the tablet computer to both examination systems 1, 1a.

From the received examination data, the computing unit 21 creates display data D1, D2 and sends it to the display 25, where it is displayed. Shown here on the display 25 is an avatar A of a patient O. This avatar enables a better localization of the regions of examination.

Furthermore, the computing unit 21 creates control data CD from instructions from a user provided on the touchscreen and sends the control data CD to the medical examination systems 1, 1a.

Figure 3:
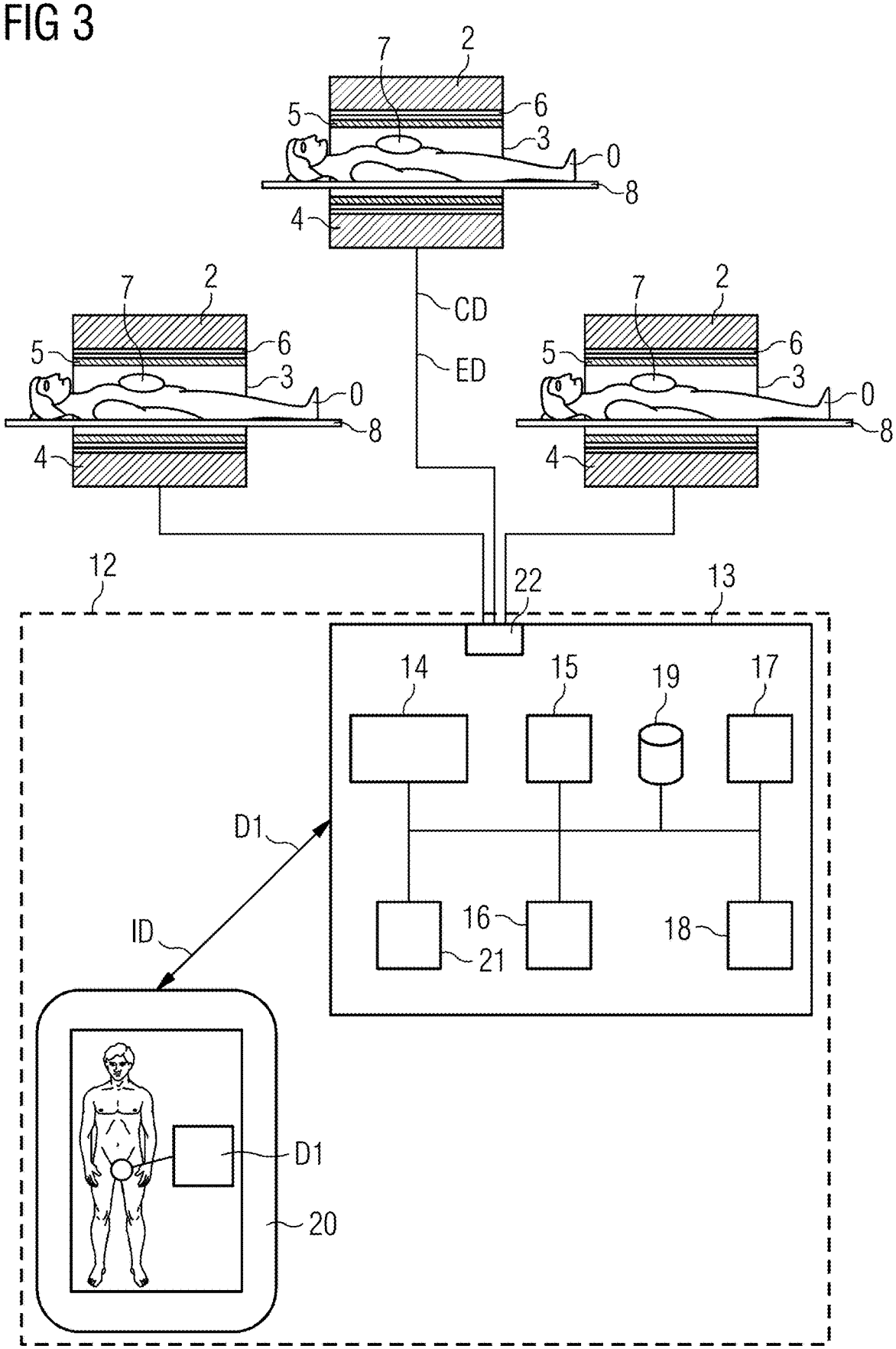
FIG. 3 shows another simplified aspect according to the disclosure.

FIG. 3 shows another simplified aspect according to the disclosure. The tablet computer should comprise the same components as shown in FIG. 2, although they are not shown here. The communication interface 22 of the tablet shown in FIG. 2 is here not used as communication interface of the user interface, but as data interface for an internal communication of the user interface 12.

In contrast to FIG. 2, the user interface 12 is here formed by the device 20 and a control unit 13 (e.g. in form of a cloud service). The control unit is connected with three scanners 2 and is able to control these scanners 2.

Here it is assumed, that the patient associated with the device 20 is examined in the upper scanner 2. If an operator starts the examination, e.g. with a touch on the touchscreen, the respective input data ID is created and sent from the tablet computer to the control device 13. Then the control unit 13 of the user interface 12 sends control data CD to the upper scanner 2 via the communication interface 22, e.g. the instruction "start examination". After the examination, the user interface 12 receives examination data ED from the upper scanner 2 via the communication interface 22. Then, a computing unit 21 creates display data D1 and sends it to the tablet computer, where it is displayed.

Figure 4:
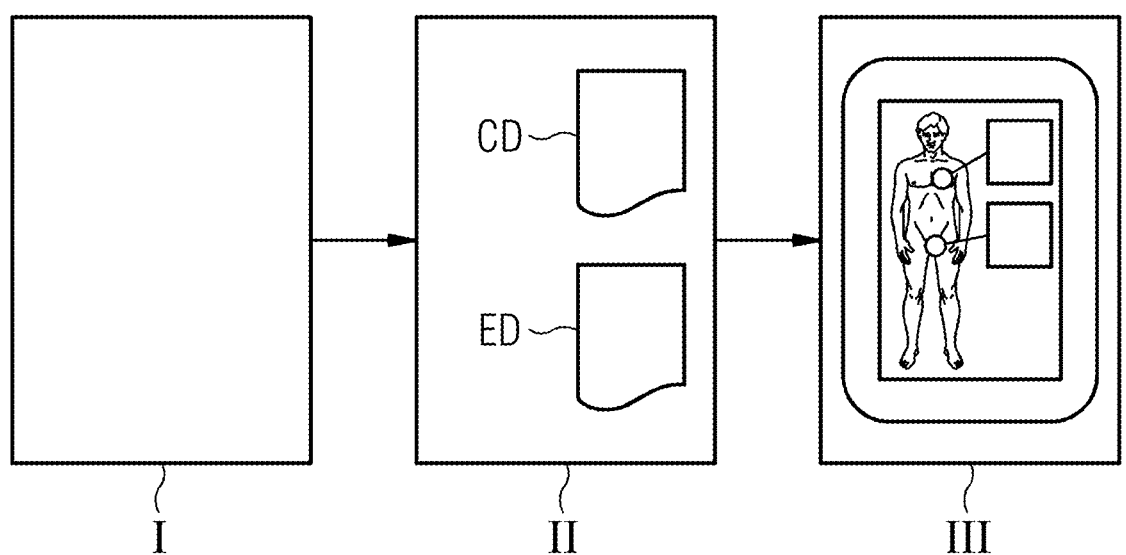
FIG. 4 shows a block diagram of the process flow of a preferred method according to the disclosure.

FIG. 4 shows a block diagram of the process flow of a preferred method designed to operate a medical user interface according to the disclosure. In the following a system as shown in FIG. 2 or 3 is regarded.

In step I, the state of an input device (e.g. a touch screen) is determined and in the case an instruction of a user is received, an output is produced based on the instruction. For example, if an operator points on the "Start" button on a touchscreen to start an examination with a special scanner 2, input data ID is created in order to produce control data CD to be sent to the scanner 2.

In step II, the control data is sent to a medical examination system 1, 1a and/or medical examination data ED is received from a medical examination system 1, 1a and processed.

In step III, the processed medical examination data ED is displayed. Alternatively or additionally, data from a medical examination system 1, 1a is displayed in form of display data D1, D2.

Although the present disclosure has been disclosed in the form of preferred aspects and variations thereon, it will be understood that numerous additional modifications and variations could be made thereto without departing from the scope of the disclosure. For the sake of clarity, it is to be understood that the use of "a" or "an" throughout this application does not exclude a plurality, and "comprising" does not exclude other steps or elements. The mention of a "unit" or a "device" does not preclude the use of more than one unit or device.

The invention claimed is:

1. A medical user interface for the combined use of at least two medical examination systems, comprising:
   a display data interface configured to connect to a display and to send medical display data to be displayed on the display;
   an input data interface configured to connect to an input device for receiving instructions of a user;
   a communication interface configured to data connect with the at least two medical examination systems; and
   a computer configured to:
      establish a data communication to the at least two medical examination systems via the communication interface, and to receive, from a first medical examination system of the at least two medical examination systems, a first set of examination data associated with a first examination of a patient;
      track a state of a patient using sensor data;
      process the instructions received from the user;
      perform an automatic segmentation of image data obtained via the first set of examination data to identify a body tissue compartment of the patient;
      compute, using rendered compartment borders resulting from the segmentation of the image data, a predefined sampling pattern to enable acquisition, via a second examination of the patient, a second set of examination data of the body tissue compartment of the patient at a lower resolution than the first set of examination data;
      transmit control data to a second medical examination system of the at least two medical examination systems, the control data identifying a configuration to be used by the second medical examination system to perform the second examination of the patient to acquire the second set of examination data using the predefined sampling pattern;
      generate the display data based upon the first set of medical examination data and the second set of medical examination data; and
      transmit the display data to the display rendered to the current state of the patient.

2. The medical user interface according to claim 1, wherein the medical user interface is configured to operate in accordance with:
   a patient mode, wherein access to a number of medical examination systems is restricted and examination data is collected for an individual patient; or an operator mode, wherein access to the medical examination systems and access to patient data is restricted according to access rights of a specific user.

3. The medical user interface according to claim 1, further comprising:
a data interface configured to access the sensor data from a camera, a GPS-sensor, a gyroscope, an RFID-sensor, or a sensor of a mobile computing or telecommunication device to enable the computer to track the motion state of the patient.

4. A method for operating a medical user interface, comprising:
providing the medical user interface for the combined use of at least two medical examination systems including (i) a display data interface configured to connect to a display and to send medical display data to be displayed on the display, (ii) an input data interface configured to connect to an input device for receiving instructions of a user, (iii) a communication interface configured to data connect with the at least two medical examination systems, and (iv) a computer, the method comprising:
establishing a data communication to the medical examination systems via the communication interface;
receiving, from a first medical examination system of the at least two medical examination systems, a first set of examination data associated with a first examination of a patient;
track a state of a patient using sensor data;
performing an automatic segmentation of image data obtained via the first set of examination data to identify a body tissue compartment of the patient;
compute, using rendered compartment borders resulting from the segmentation of the image data, a predefined sampling pattern to enable acquisition, via a second examination of the patient, a second set of examination data of the body tissue compartment of the patient at a lower resolution than the first set of examination data;
transmitting control data to a second medical examination of the at least two medical examination systems, the control data identifying a configuration to be used by the second medical examination system to perform the second examination of the patient to acquire the second set of examination data in accordance with the predefined sampling pattern;
generating display data based upon the first set of medical examination data and the second set of medical examination data; and
transmitting the display data to a display rendered to the current state of the patient.

5. The method according to claim 4, further comprising:
processing and displaying patient specific information initially or in addition to the first examination,
wherein the patient is represented as a patient model or as an avatar.

6. The method according to claim 4, wherein the act of tracking the state of the patient comprises:
tracking a position of the patient, or
tracking examination or accommodation stations of the patient.

7. The method according to claim 4, further comprising:
adding the second set of examination data of the patient to the first set of examination data; and
combining a part of the second set of examination data with a part of the first set of examination data with an individual time stamp,
wherein the part of the second set of examination data and the part of the first set of examination data pertain to a same medical environment, a same disease, a same body region, or a same examination procedure.

8. The method according to claim 7, wherein:
the second set of examination data represent a difference of a current patient state according to the first examination data,
the difference is measured directly based on the first examination data or calculated from the second examination data and the first examination data, and
the second examination data are acquired with a point of care scanner or in the course of a point of care examination.

9. The method according to claim 8, further comprising:
applying, in the course of the second examination, spatial localization with an optimal pointspread function.

10. A device, comprising:
a medical user interface for the combined use of at least two medical examination systems including:
a display data interface configured to connect to a display and to send medical display data to be displayed on the display:
an input data interface configured to connect to an input device for receiving instructions of a user;
a communication interface configured to data connect with the at least two medical examination systems; and
a computer configured to:
establish a data communication to the at least two medical examination systems via the communication interface, and to receive, from a first medical examination system of the at least two medical examination systems, a first set of examination data associated with a first examination of a patient;
track a state of a patient using sensor data;
perform an automatic segmentation of image data obtained via the first set of examination data to identify a body tissue compartment of the patient;
compute, using rendered compartment borders resulting from the segmentation of the image data, a predefined sampling pattern to enable acquisition, via a second examination of the patient, a second set of examination data of the body tissue compartment of the patient at a lower resolution than the first set of examination data;
transmit control data to a second medical examination of the at least two medical examination systems, the control data identifying a configuration to be used by the second medical examination system to perform the second examination of the patient to acquire the second set of examination data in accordance with the predefined sampling pattern;
generate the display data based upon the first set of medical examination data and the second set of medical examination data; and
transmit the display data to the display rendered to the current motion state of the patient.

11. The device according to claim 10, wherein the device is configured to be attachable to and detachable from one of the at least two medical examination systems, and to accompany the patient while moving within a clinical environment, or to be mountable on a patient bed.

12. A non-transitory computer-readable medium having stored thereon program elements that, when executed by a computer, cause the computer to perform steps of the method according to claim 4.

13. The medical user interface of claim 1, wherein the computer is further configured to track a position of the patient or a position of an operator.

14. The medical user interface of claim 1, wherein the patient state comprises a patient motion state, and wherein the computer is further configured to continue to track the patient motion state as the patient moves between different ones of the at least two medical examination systems.

15. The method of claim 4, wherein the patient state comprises a patient motion state, and further comprising:
   continuing the tracking of the patient motion state as the patient moves between the at least two medical examination systems.

16. The device of claim 10, herein the patient state comprises a patient motion state, and further comprising:
   continuing the tracking of the patient motion state as the patient moves between the at least two medical examination systems.

17. The medical user interface of claim 1, wherein the computer is configured to send the display data to the display rendered to the current state of the patient such that the first set of medical examination data is displayed while the second set of examination data is being acquired.

18. The medical user interface of claim 1, wherein the computer is configured to determine the predefined sampling pattern by comparing data associated with the body tissue compartment with predefined reference information identified with a set of predefined sampling patterns, and selecting, as the predefined sampling pattern, one of the predefined sampling patterns identified with reference information having the highest similarity with the data associated with the body tissue compartment.

19. The medical user interface of claim 1, wherein the computer is configured to create the display data based upon the first set of medical examination data and the second set of medical examination data such that the display data includes a patient model that is updated with information obtained using the second set of medical examination data.

\* \* \* \* \*